(12) United States Patent
Ström

(10) Patent No.: US 6,533,730 B2
(45) Date of Patent: Mar. 18, 2003

(54) METHOD FOR ASSESSING PULMONARY STRESS AND BREATHING APPARATUS EMPLOYING THE METHOD

(75) Inventor: Christer Ström, Piteå (SE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 09/736,346

(22) Filed: Dec. 15, 2000

(65) Prior Publication Data

US 2001/0004677 A1 Jun. 21, 2001

(30) Foreign Application Priority Data

Dec. 17, 1999 (SE) ................................................ 9904643

(51) Int. Cl.⁷ ................................................ A61B 5/08
(52) U.S. Cl. ........................ 600/533; 600/529; 600/543; 128/202.22
(58) Field of Search ................................ 600/529, 533, 600/538, 543; 128/200.24, 202.22, 204.21

(56) References Cited

U.S. PATENT DOCUMENTS

| | | | | |
|---|---|---|---|---|
| 3,621,833 A | * | 11/1971 | Crane | ......................... 600/533 |
| 4,267,845 A | * | 5/1981 | Robertson, Jr. et al. | .... 128/721 |
| 4,351,344 A | * | 9/1982 | Stenzler | ....................... 128/720 |
| 4,393,869 A | | 7/1983 | Boyarsky et al. | |
| 4,802,492 A | * | 2/1989 | Grunstein | .................... 128/720 |
| 5,875,777 A | * | 3/1999 | Eriksson | ................. 128/204.21 |
| 6,192,885 B1 | * | 2/2001 | Jalde | ......................... 128/204.1 |

FOREIGN PATENT DOCUMENTS

| | | |
|---|---|---|
| EP | 0 671 180 | 9/1995 |
| EP | 0 691 134 | 1/1996 |
| EP | 0 776 672 | 6/1997 |
| FR | 2 666 012 | 2/1992 |
| GB | 2 077 444 | 12/1981 |
| WO | WO 87/00928 | 2/1987 |

* cited by examiner

*Primary Examiner*—Charles G. Freay
*Assistant Examiner*—John Belena
(74) *Attorney, Agent, or Firm*—Schiff Hardin & Waite

(57) ABSTRACT

In a method for assessing pulmonary stress, a flow of respiratory gas is supplied to the lungs of a subject, an ensuing pressure is measured in relation to time and the pressure-time relationship is analyzed. In this analysis, the profile of the pressure-time relationship is determined. In summary, the profile is straight when no stress is present, is convex when there is a risk for over-distension, and is concave when alveolar units are opened up. Implemented in a breathing apparatus the method can be used to assist an operator in diagnostic and therapeutic considerations in relation to a patient.

18 Claims, 1 Drawing Sheet

METHOD FOR ASSESSING PULMONARY STRESS AND BREATHING APPARATUS EMPLOYING THE METHOD

BACKGROUND OF THE INVENTION

1. Field of the Invention

The present invention is directed to a method and an apparatus for assessing pulmonary stress in a respirating subject.

2. Description of the Prior Art

In U.S. Pat. No. 4,351,344 a method and apparatus for monitoring lung compliance is disclosed. A constant flow of gas is supplied during inspiration and a pressure versus time relationship is recorded. The pressure-time relationship is analyzed with respect to linearity. More specifically, the temporal length of a linear slope segment in the pressure-time relationship is determined. The temporal length can be compared with limits and an indication of the compliance status for the patient can be made based on the comparison.

The information thus obtained is, however, insufficient and inconclusive for being properly used in determinations of the status of the lung and as a tool for improving treatment of a lung.

Mechanical ventilation is used as a life saving treatment in many circumstances. But it can also aggravate pre-existing disease and even induce lung injury if the dynamics and physiology of mechanical breath delivery are not considered.

The lung has an inherent tendency to collapse. During normal breathing this tendency is counteracted by the chest wall and a natural substance called surfactant.

In the case of disease, the collapsing tendency becomes more pronounced, giving rise to areas (alveolar units) that collapse early during exhalation/expiration and open late during inhalation/inspiration. This cyclic opening and closing of airways may initiate lung injury manifested as gross air leaks, diffuse alveolar damage, pulmonary edema and pulmonary inflammation, all of which have been termed Ventilator Induced Lung Injury (VILI). The cyclical opening and closing of alveolar units can be counteracted by the administration of a correctly set Positive End Expiratory Pressure (PEEP).

A second postulated mechanism for VILI is the delivery of large tidal volumes (which can cause volutrauma) or high end inspiratory airway pressure (which can cause barotrauma). Both may over-stretch lung tissues, leading to fluid accumulation, inflammation and increased stiffness of the lung. Baro-/volutrauma can be avoided by setting a proper tidal volume or peak pressure.

If the ventilator settings are not optimized, the period before VILI can be considered as a period of increased stress. Hence, a determination of the degree of lung stress that may follow from a specific ventilator setting can be considered as a pulmonary stress index (PSI).

SUMMARY OF THE INVENTION

It is an object of the invention to provide a method for assessing the pulmonary stress induced by the ventilatory settings for any particular patient, in particular using pulmonary stress index (PSI). PSI can be an important tool in the course of diagnosing the condition of a lung and also for determining a proper treatment causing a minimum of harm to a subject.

It is another object of the invention to provide a breathing apparatus that can perform assessments of pulmonary stress and PSI.

It is a further object of the invention to provide a breathing apparatus that can be used for obtaining a more beneficial treatment of subjects with a minimum of VILI.

This object is achieved in the inventive method by obtaining a pressure-time relationship based on a gas flow supplied to the lungs of a subject, and analyzing the profile (curve shape) of the relationship. By analyzing the profile of the relationship, important information can be extracted. In particular, determining convexity or concavity of the profile provides relevant information.

One advantageous analysis is to adopt the profile to a power equation, e.g in the form of $P_{ao}=a*t^b+c$, where $P_{ao}$ is pressure, t is time and a, b and c are constants. Determination of the constant b is particularly interesting since b is a determinant of the shape of the profile. If b equals 1, the profile consists of a straight line, if b is less than 1 the profile is concave and if b is higher than 1 the profile is convex.

Convex profiles have been found to correspond to risks of progressive over-distension of lungs (decreasing compliance) and concave profiles have been found to correspond to risks associated with cyclic closing and opening of alveolar units (increasing compliance). Profiles can also be sigmoidal, i.e., include both concave and convex portions.

Analysis can be performed on pressure-time relationship on a breath-by-breath basis or on averaged values over a number of breaths.

Another advantageous analysis to adopt the profile to a polynomial equation, e.g. in the form of $P_{ao}=\alpha+\beta*t+\gamma*t^2$, where $P_{ao}$ is pressure, t is time and $\alpha$, $\beta$ and $\gamma$ are constants. Determination of the constant $\gamma$ is particularly interesting since $\gamma$ is a determinant of the shape of the profile. If $\gamma$ equals O, the profile consists of a straight line, if $\gamma$ is less than 0 the profile is concave and if $\gamma$ is higher than 0 the profile is convex.

An inventive breathing apparatus that achieves the above objects has a gas regulator for regulating respiratory gas flows, a pressure gauge for (directly or indirectly) measuring a pressure, preferably the airway pressure and a control unit for controlling the gas regulator to at least supply a constant flow of a respiratory gas during inspiration phases while measuring pressure in relation to time. The control unit is further adapted to perform the methods described above.

In one preferred embodiment, the control unit is adapted to compare the constant b with an interval, preferably with a lower limit between 0.5 and 0.95 and an upper limit between 1.05 and 1.5. As long as the constant b falls within the interval, there is no pulmonary stress. If the constant b falls outside the interval there is pulmonary stress. The value of the constant b thus provides both an indication of the presence of pulmonary stress and the magnitude of it. The constant b can therefore be used as a value for pulmonary stress index, PSI.

Similar results are obtained when the constant $\gamma$ is used.

In another preferred embodiment, the apparatus has a display unit and an alarm unit. The control unit is further adapted to perform at least one out of a plurality of actions depending on e.g. the value of the constant b or $\gamma$ (pulmonary stress index). It can generate an alarm when the stress index is too high or too low, indicating that a possibly injurious therapy is being delivered to a subject. It can display the stress index, as well as the P-t relationship, on the display unit. It can calculate suitable changes in control parameters for reducing pulmonary stress and display these as options for an operator on the display unit. It can automatically re-set the control parameters in accordance with calculations of suitable changes in the control parameters. It can determine if recruiting maneuvers should be provided, and can recommend/automatically perform recruiting maneuvers, etc.

The apparatus according to the invention can advantageously be used for automatic re-setting of PEEP, tidal volume, airway pressure, I:E ratio otherventilator-controlled parameters.

A further version of the inventive breathing apparatus that achieves the above objects has at least a first gas regulator and a second gas regulator for regulating a respiratory gas flow, at least one pressure gauge and a control unit for controlling the gas regulator based on set control parameters and for establishing a pressure-time(P-t) relationship.

To achieve a proper treatment, with a minimum of stress to the lungs, the control unit is adapted to perform a series of actions, corresponding to phases.

During the first phase, the control unit controls the first gas regulator and second gas regulator to provide respiration cycles having an initial tidal volume, an initial respiratory rate, an initial inspiratory time in relation to total respiration cycle time, a constant inspiratory gas flow, an initial oxygen fraction and an initial PEEP value. All the initial values can be predefined within the control unit, calculated by the control unit based on patient information, e.g. weight, diagnosis, etc., or entered via an operator interface by an operator.

During the second phase, the control unit controls the first gas regulator and second gas regulator to provide a progressive increase of the initial PEEP value and to determine the stress index. The stress index (e.g. constant b or g) is compared with a predefined interval and when the stress index falls within the predefined interval, the control unit can proceed to the next phase.

During the third phase, the control unit controls the first gas regulator and second gas regulator to provide at least one recruiting manoeuvre having a specific inflation pressure and inflation time. The inflation pressure could be up to levels of 30–40 cmH$_2$O or even higher if necessary. The stress index is determined and compared with the predefined interval. If the stress index falls below the predefined interval, the control unit controls the apparatus to provide a further progressive increase of the PEEP value and repeat the recruiting maneuver(s). This is continued, until the stress index exceeds the predefined interval. Thereafter, the next phase can be commenced.

During the fourth phase, the control unit continues to determine the stress index and compare it with the predefined interval. At the same time it controls the first gas regulator and the second gas regulator to provide a progressive decrease in the PEEP value. This is continued until the stress index falls within the predefined interval.

The result of all these phases is that a setting for the apparatus is achieved that does not stress the patient. Through the operator interface, an operator can repeat the entire sequence or specific phases. It can also be beneficial if the onset of some phases requires initialisation from the operator, whereby the control unit can be adapted to display requests for proceeding on the operator interface.

DESCRIPTION OF THE PREFERRED EMBODIMENTS

Figure 1:
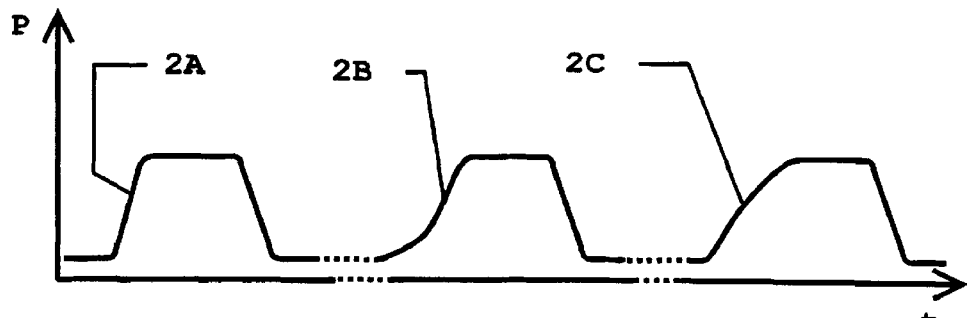
FIG. 1 shows in a pressure-time diagram three different types of respiration profiles.

FIG. 1 shows three different respiratory cycles in a pressure-time diagram P-t. The cycles have been obtained by measuring the pressure during constant flow inspiration, pause and expiration. The first cycle has a profile 2A during inspiration that is essentially straight, the second cycle has a profile 2B during inspiration that is convex and the third cycle has a profile 2C during inspiration that is concave.

Similar curves could be obtained by determining actual lung pressure during supply of gas with a constant pressure. Determination of actual lung pressure can be made by measuring pressure within the lungs (e.g. at or near carina) or by calculating the pressure within the lungs with known methods.

The present invention is thus applicable for all situations where gas is supplied to a subject.

According to the method of the present invention, helpful information can be obtained from the profiles 2A–C. In particular, the convexity or concavity of the profile will provide essential information.

One way of analyzing the profiles 2A–C is to adapt each profile to a power equation, e.g. $P_{ao}=a*t^b+c$. $P_{ao}$ represents airway pressure or $P_{tp}$, but need not necessarily be measured at the airway opening. Pressure can be measured elsewhere and the airway pressure can be estimated from the measured pressure. t represents time and a, b and c are constants (for any specific profile). In particular constant b is here of interest, since it is a determinant for the shape of the profile. If b=1, the profile is straight, as in profile 2A, if b>1, the profile is convex, as in profile 2B and if b<1, the profile is concave, as in profile 2C.

It is of course possible to apply other mathematical algorithms for determining the profiles. One alternative is to apply a polynomial function, e.g. $P_{ao}=\alpha+\beta*t+\gamma*t^2$. In this case, the constant $\gamma$ is the most interesting, since it determines whether the profile is convex, concave or straight. Higher orders of polynomial functions also can be used.

Other tools are also possible to use. For instance, a straight line can be applied between the first and last coordinates of the P-t relationship. If the profile is convex (or essentially convex), most or all coordinates will lie below the straight line. If the profile is concave (or essentially concave), most or all co-ordinates will lie above the straight line. A weighting of measured data thus provides the result. Profiles having a sigmoidal shape can be stepwise analyzed and provide indication on presence of both convex and concave parts (several values for b). An essentially straight profile will have its co-ordinates fairly evenly distributed on both sides of the straight line.

It may here be noted that when a constant flow of gas is supplied to the subject a pressure-volume relationship will provide the same information as the P-t relationship and may therefore be used instead. (Or, to put it another way, the pressure-volume relationship is really a pressure-time relationship since the volume V is equal to the constant flow $\Phi$ multiplied with time t; $V=\Phi*t$.) It does not matter whether pressure is used on the y-axis or x-axis (with time or time-related variable on the other), when illustrated in a diagram.

The profiles can also be analyzed by using artificial neural networks (ANN), pattern recognition systems, etc.

Returning now to the analysis described above, with b-values indicating one of the three profiles 2A–C.

The convex profile 2B is an indication of a decrease in compliance with increasing tidal volumes. Such decrease is correlated to progressive over-distension. This basically means that the physical limit for expansion of the ventilated alveolar units has been reached. Treatment at this level may not only cause physical injury to lung tissue, but may also have detrimental effects on blood circulation through the lungs.

The concave profile 2C is an indication of an increase in compliance with increasing tidal volumes. Such increase is correlated to the opening up of alveolar units within the lungs. If a treatment were to display this kind of profile breath after breath (or as an average over a plurality of breaths), it is a sign of cyclic closing and opening of alveolar units. Such treatment is not ideal and may be injurious to the lungs.

In other words is it beneficial to the patient to arrive at a treatment where the straight profile 2A predominates. This means situations where b≈1.

Based on this, the constant b can be used as an indication of the pulmonary stress. With b as a pulmonary stress index (PSI), the value of the stress index can be used to inform an operator of pulmonary stress. Since there are always variations in the real world, a normal or minimal stress index can be allowed to vary within a predefined interval. The interval could e.g. be 0.9–1.1. The interval can be set by an operator before starting a treatment.

Figure 2:
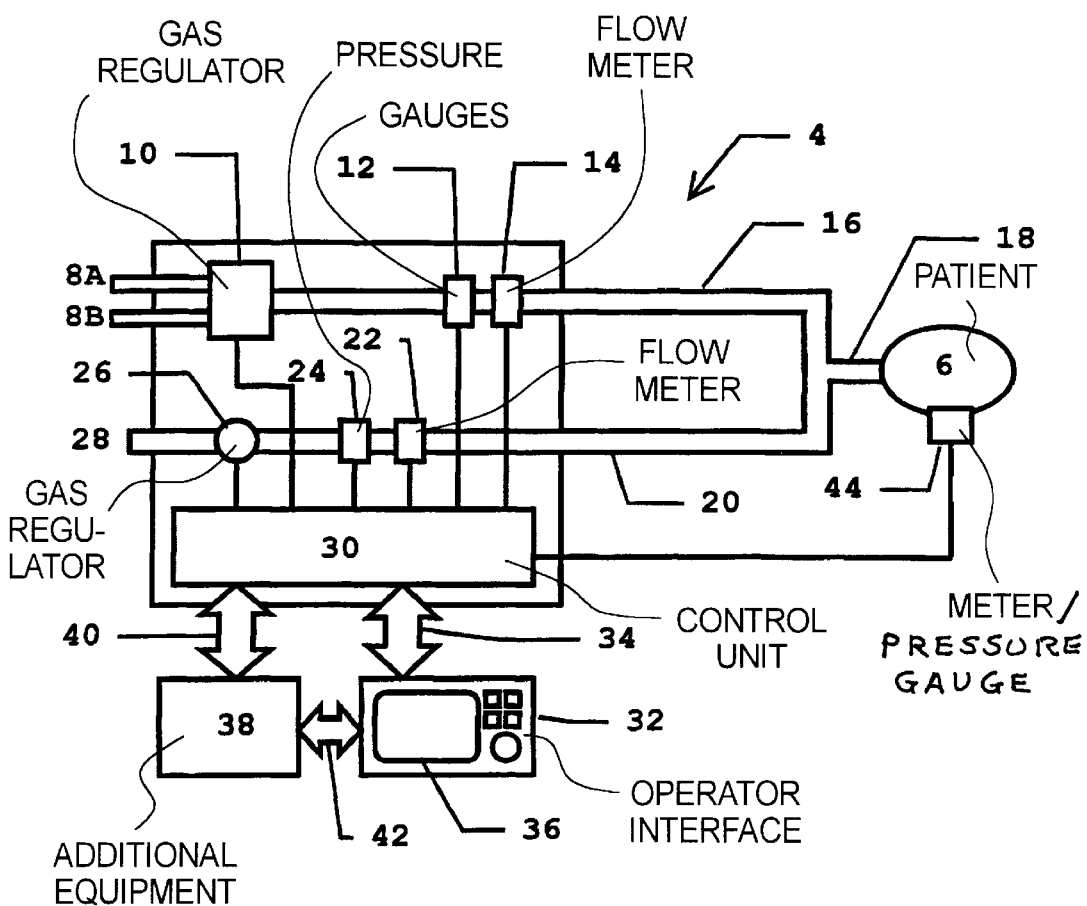
FIG. 2 shows a preferred embodiment of a breathing apparatus according to the invention.

Referring now to FIG. 2 which shows a breathing apparatus according to the invention. The breathing apparatus is generally indicated with numeral 4. The apparatus 4 can be connected to a subject, or patient 6. Essentially any animal with lung-dependent respiration can be contemplated as patient.

Gases can enter the apparatus 4 via a first gas inlet 8A and a second gas inlet 8B. The gases are then mixed into a selected respiratory gas in a first gas regulator 10. One gas inlet would be sufficient if the respiratory gas was mixed outside the apparatus 4. More gas inlets can be used where the respiratory gas is to consist of more than two gases. In this embodiment air and oxygen are used as gases.

The gas regulator 10 also regulates pressure and flow of the respiratory gas. The gas regulator 10 normally includes one or more valves for regulating down high-pressure gases, but in portable breathing apparatuses the regulator could also consist of a fan, compressor or similar device for generating a gas flow.

After the gas regulator 10, the respiratory gas passes a first pressure gauge 12 and a first flow meter 14. It then passes through an inspiration line 16 to a patient line 18 and into the patient 6.

From the patient 6 the respiratory gas will flow back through the patient line 18, into an expiration line 20 and via a second flow meter 22, a second pressure gauge 24 and a second gas regulator 26 to a respiratory gas outlet 28. The second gas regulator 26 is normally used to control respiratory gas flow during expiration for upholding a set end pressure (Positive End Expiratory Pressure—PEEP).

The pressure gauges 12, 24 and flow meters 14, 22 need not be located as shown. They can, for instance, be built in within the gas regulators 10, 26. They can also be located elsewhere in the gas flow paths of the apparatus (such as inspiration line 16 and/or patient line 18 and/or expiration line 20). In particular is it possible to locate a meter/pressure gauge 44 within the patient 6 to measure lung or airway pressure. However, based on measurements from pressure gauges 12, 24 and flow meters 14, 22 as shown, corresponding values of e.g. airway pressure can be calculated in known manner.

The operation of the first gas regulator 10 and the second gas regulator 26 is controlled by a control unit 30. The control unit 30 also receives information from the pressure gauges 12, 24, 44 and flow meters 14, 22. Based on the measured information the control unit 30 can, inter alia, determine the above disclosed stress index. The control unit 30 can be formed by any combination of known control components. It can, for instance, be a microprocessor-based system including one or several processors and memories. Software programming can be used for carrying out the functions. It could also by formed by, or include, hardware components such as EPROMs or similar. Other functions and tasks that the control unit 30 can perform are discussed below.

Via an operator interface 32 an operator of the apparatus 4 can communicate with, mainly, the control unit 30 via a first communication link 34. A display 36 can show programmed parameters, selectable functions and parameters as well as diagrams, suggested parameters, parameter cycles, stress index and other information. The display 36 can be a CRT-screen, flat screen with or without touch sensitivity, plasma screen or any suitable screen for displaying images. The display 36 need not be integrated with the operator interface 32 and several displays can be used for one apparatus 4.

Additional equipment (e.g. further displays, PC, Intranet link to databases or remote monitoring stations, Internet link, etc.) is generally designated 38 and can be connected to the apparatus 4 for communication. It can be connected to the control unit 30 via a second communication link 40 and/or to the operator interface 32 via a third communication link 42.

One example of how the apparatus 4 can be used for a patient 6 will now be described.

Suppose that a patient 6 having partially or completely collapsed lungs is connected to the apparatus 4. Although keeping the patient 6 alive is the primary goal, it should be done with minimum risk of causing further damage to the lungs. The control unit 30 is therefore programmed/constructed to perform a number of actions. These actions can be divided into phases, which can be carried out automatically or at the initiative of an operator.

The first phase is connected essentially of life maintaining measures. The control unit 30 controls the first gas regulator 10 and second gas regulator 26 to provide respiration cycles having an initial tidal volume, an initial respiratory rate, an initial inspiratory time in relation the respiration cycle time, an initial oxygen fraction ($FiO_2$) and an initial PEEP value.

The initial values can be pre-programmed into the control unit 30, but are preferably either entered by the operator via the operator interface 32 or calculated by the control unit 30 based on patient data such as age, weight, diagnosis, or other available information regarding the status of the patient. $FiO_2$ could e.g. initially be set to 100%.

During the respiration cycles the control unit 30 also determines the stress index on a regular basis and compares the stress index with the predefined interval mentioned above. The interval can have a lower limit of about 0.6–0.95 and an upper limit of about 1.05–1.4, or any other interval that is reasonable in view of the initial condition of the patient 6. In the current example of a patient 6 with collapsed lungs, the stress index will most likely fall below the predefined interval.

The second phase is basically meant to start to open up the lungs. The control unit 30 will then proceed by (mainly) controlling the second gas regulator 26 to achieve a progressive increase in PEEP. The increase will continue until the stress index exceeds the lower limit, i.e. falls within the predefined interval. The increments by which PEEP is increased can be pre-programmed, calculated by the control unit 30 or entered by the operator.

In the third phase, proper opening up of the lungs is the aim. To do this one or more recruiting maneuvers are performed by the apparatus 4. A recruiting maneuver essentially consists of a prolonged inspiration (or rather inflation) at an elevated pressure in relation to the initial settings. The inspiration can last up to about a minute and the pressure can be up to 40–60 cmH$_2$O. Again, the values can be higher or lower depending on the specific circumstances that prevail. Control parameters for the recruiting maneuver can be pre-programmed, calculated by the control unit 30 or entered by the operator. Other recruiting maneuvers also can be used.

After the recruiting maneuver(s) stress index is again determined and compared with the predefined interval. Should the stress index be lower or even within the interval (but not optimal), the control unit 30 will control the second gas regulator 26 to increase PEEP again.

Another recruiting maneuver or maneuvers is then supplied, followed by new determination of stress index.

This procedure of recruiting maneuver(s) and increase of PEEP value continues until stress index exceeds the upper limit of the predefined interval. This means that the lung has been fully recruited and can be regarded as fully open.

The fourth phase aims at reaching a proper setting for PEEP. The control unit 30 therefore controls the apparatus 4 to decrease PEEP, while determining stress index. When stress index falls within the interval, the settings regarding PEEP are essentially optimized.

Since the lungs are open, FiO$_2$ can be lowered. A proper decrease of FiO$_2$ is made when saturation of oxygen is decreased by 1–2%. A meter 44 for saturation and, if required, obtaining other patient data is shown in FIG. 2. The decrease can be performed by the operator or by the control unit 30 (requiring access to saturation measurements).

When the operator wishes to select another respiration mode, the control unit 30 can display the determined no stress setting on the display 36 as a suggestion to the operator.

A similar procedure can of course be performed when the profile of the P-t relationship is analyzed in other ways (as described in connection with the method according to the invention). The profile will inevitably display convexity when there is a risk for over-distension and concavity when alveolar units are being opened.

Although not explicitly mentioned above, the breathing apparatus can of course be constructed or adapted to perform or carry out additional functions, as are known to persons skilled in the art.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for assessing pulmonary stress, comprising the steps of:
    connecting a respirating subject to an inspiration/expiration gas flow path;
    supplying respiratory gas to said subject's respiratory system via said flow path;
    measuring pressure in relation to time in one of said respiratory system and said gas flow path; and
    assessing pulmonary stress of said subject by determining a profile of said pressure-time relationship of gas in said gas flow path.

2. A method as claimed in claim 1 wherein the step of determining said profile comprises determining a convexity/concavity of said profile.

3. A method as claimed in claim 2 wherein the step of determining said profile comprises adapting said pressure-time relationship to a power equation $P_{ao}=a*t^b+c$, wherein $P_{ao}$ is pressure, t is time, and a, b and c are constants, and determining at least the constant b as a determinant for said profile, by determining said profile to be concave if b<1 indicative of an increase in lung compliance, determining said profile to be straight if b=1 indicative of a constant lung compliance, and determining said profile to be convex if b>1 indicating a reduction in lung compliance.

4. A method as claimed in claim 2 wherein the step of determining said profile comprises adapting said pressure-time relationship to a polynomial equation $P_{ao}=\alpha+\beta*t+\gamma*t^2$, wherein $P_{ao}$ is pressure, t is time, and $\alpha$, $\beta$ and $\gamma$ are constants, and determining at least the constant $\gamma$ as a determinant for said profile, whereby said profile is concave if $\gamma<0$ indicative of an increase in lung compliance, said profile is straight if $\gamma=0$ indicative of a constant lung compliance, and said profile is convex if $\gamma>0$ indicative of a reduction in lung compliance.

5. A method as claimed in claim 1 comprising determining said profile during each breath of said subject.

6. A method as claimed in claim 1 comprising determining said profile as an average over a plurality of breaths of said subject.

7. A breathing apparatus comprising:
    an inspiration/expiration gas flow path adapted for connection to a respirating subject's respiratory system;
    a gas regulator connected in said gas flow path for regulating respiratory gas flow in said gas flow path;
    a pressure gauge for measuring pressure in one of said respiratory system and said gas flow path; and
    a control unit connected to said pressure gauge and to said gas regulator for determining a profile of a pressure-time relationship of gas in said gas flow path from said pressure measured by said pressure gauge, and for assessing pulmonary stress and operating said gas regulator dependent on said profile.

8. A breathing apparatus as claimed in claim 7 wherein said control unit determines a convexity/concavity of said profile.

9. A breathing apparatus as claimed in claim 8 wherein said control unit determines said profile by adapting said pressure-time relationship to a power equation $P_{ao}=a*t^b+c$, wherein $P_{ao}$ is pressure, t is time, and a, b and c are constants, by determining at least the constant b as a determinant for said profile, and wherein said control unit determines said profile is concave if b<1 indicative of an increase in lung compliance, determines said profile is straight if b=1 indicative of a constant lung compliance, and determines said profile is convex if b>1 indicative of a reduction in lung compliance.

10. A breathing apparatus as claimed in claim 9 wherein said control unit compares the determined constant b with a predefined interval and analyzes said pulmonary stress as being a minimum if b is within said interval, analyzes an existence of pulmonary stress due to alveolar opening and closing to be present if b is below said predefined interval, and determines alveolar over-distension to be present if b is above said interval.

11. A breathing apparatus as claimed in claim 10 comprising defining said predefined interval for the constant b as having a lower limit between 0.5 and 0.95 and an upper limit between 1.05 and 1.5.

12. A breathing apparatus as claimed in claim 8 wherein said control unit determines said profile by adapting said pressure-time relationship to a polynomial equation $P_{ao}=\alpha+\beta*t+\gamma*t^2$, wherein $P_{ao}$ is pressure, t is time, and $\alpha$, $\beta$ and $\gamma$ are constants, and wherein said control unit determines at least the constant $\gamma$ as a determinant for said profile and wherein said control unit compares the determined constant $\gamma$ with a predefined interval and determines a minimum of pulmonary stress to be present if $\gamma$ is within said interval, determines pulmonary stress due to alveolar opening and closing to be present if $\gamma$ is below said interval, and determines alveolar over-distension to be present if $\gamma$ is above said interval.

13. A breathing apparatus as claimed in claim 7 further comprising a display unit and an alarm unit, and wherein said control unit, dependent on the determination of said profile, initiates at least one action selected from the group of actions consisting of generating an alarm via said alarm unit, generating a warning on said display that pulmonary stress is present, determining a change in at least one control parameter for said gas regulator, determining a change in at least one control parameter for said gas regulator and displaying the determined change on said display, determining a change in at least one control parameter for said gas regulator and automatically resetting said at least one control parameter dependent on said change, displaying a recommendation for a recruiting maneuver on said display, and automatically performing a recruiting maneuver.

14. A breathing apparatus as claimed in claim 13 wherein said control parameter is selected from the group consisting of positive end expiratory pressure, fraction of oxygen in said respiratory gas, and tidal volume.

15. A breathing apparatus comprising:
- an inspiration/expiration gas flow path adapted for connection to a respirating subject's respiratory system;
- a first gas regulator connected in said gas flow path and a second gas regulator connected in said gas flow path for, in combination, regulating respiratory gas flow in said gas flow path;
- a pressure gauge connected in one said respiratory system and said gas flow path for measuring pressure of said respiratory gas in said one of said respiratory system and said gas flow path;
- a control unit connected to said first gas regulator, said second gas regulator and said pressure gauge for identifying a pressure-time relationship of said respiratory gas in said gas flow path from said pressure measured by said pressure gauge and for analyzing pulmonary stress by determining a profile of said pressure time relationship;
- said control unit, in a first phase, operating said first gas regulator and said second gas regulator to provide respiration cycles having an initial tidal volume, an initial respiratory rate, an initial inspiratory time relative to a total respiration cycle time, a constant inspiratory gas flow, an initial oxygen fraction of said respiratory gas, and an initial PEEP value;
- said control unit in a second phase operating said first gas regulator and said second gas regulator to progressively increase said PEEP value from said initial PEEP value, and wherein said control unit determines said profile by adapting said pressure-time relationship to a power equation $P_{ao}=a*t^b+c$, wherein $P_{ao}$ is pressure, t is time, and a, b and c are constants, and determining at least the constant b as a determinant for said profile, and wherein said control unit compares the determined constant b to a predefined interval and if b is within said interval, said control unit proceeds to a third phase;
- in said third phase, said control unit operating said first gas regulator and said second gas regulator to execute a recruiting maneuver having a specific lung inflation pressure and a specific lung inflation time and wherein said control unit compares the determined constant b to said interval and if b is below said interval, said control unit operates said first gas regulator and said second gas regulator to further progressively increase said PEEP value and repeatedly executes said recruiting maneuver until b is within said interval; and
- in a fourth phase, said control unit compares the determined constant b to said interval and operates said first gas regulator and said second gas regulator to progressively decrease said PEEP value until b is within said interval.

16. A breathing apparatus as claimed in claim 15 further comprising an operator interface allowing an operator to set said initial tidal volume, said initial respiratory rate, said initial inspiratory time relative to said total respiration cycle time, said initial oxygen fraction in said respiratory gas and said initial PEEP value.

17. A breathing apparatus comprising:
- an inspiration/expiration gas flow path adapted for connection to a respirating subject's respiratory system;
- a first gas regulator connected in said gas flow path and a second gas regulator connected in said gas flow path for, in combination, regulating respiratory gas flow in said gas flow path;
- a pressure gauge connected in one of said respiratory system and said gas flow path for measuring pressure of said respiratory gas in said one of said respiratory system and, said gas flow path;
- a control unit connected to said first gas regulator, said second gas regulator and said pressure gauge for identifying a pressure-time relationship of said respiratory gas in said gas flow path from said pressure measured by said pressure gauge and for analyzing pulmonary stress by determining a profile of said pressure time relationship;
- said control unit, in a first phase, operating said first gas regulator and said second gas regulator to provide respiration cycles having an initial tidal volume, an initial respiratory rate, an initial inspiratory time relative to a total respiration cycle time, a constant inspiratory gas flow, an initial oxygen fraction of said respiratory gas, and an initial PEEP value;
- said control unit in a second phase operating said first gas regulator and said second gas regulator to progressively increase said PEEP value from said initial PEEP value, and wherein said control unit determines said profile by adapting said pressure-time relationship to a polynomial equation $P_{ao}=\alpha+\beta*t+\gamma*t^2$, wherein $P_{ao}$ is pressure, t is time, and $\alpha$, $\beta$ and $\gamma$ are constants, and determining at least the constant $\gamma$ as a determinant for said profile, and wherein said control unit compares the determined constant $\gamma$ to a predefined interval and if $\gamma$ is within said interval, said control unit proceeds to a third phase;
- in said third phase, said control unit operating said first gas regulator and said second gas regulator to execute a recruiting maneuver having a specific lung inflation pressure and a specific lung inflation time and wherein said control unit compares the determined constant b to said interval and if γ is below said interval, said control unit operates said first gas regulator and said second gas regulator to further progressively increase said PEEP value and repeatedly executes said recruiting maneuver until γ is within said interval; and in a fourth phase, said control unit compares the determined constant b to said interval and operates said first gas regulator and said second gas regulator to progressively decrease said PEEP value until γ is within said interval.

18. A breathing apparatus as claimed in claim 17 further comprising an operator interface allowing an operator to set said initial tidal volume, said initial respiratory rate, said initial inspiratory time relative to said total respiration cycle time, said initial oxygen fraction in said respiratory gas and said initial PEEP value.

* * * * *